US006291533B1

(12) United States Patent
Fleischner

(10) Patent No.: US 6,291,533 B1
(45) Date of Patent: Sep. 18, 2001

(54) DIETARY SUPPLEMENTS FOR EACH SPECIFIC BLOOD TYPE

(75) Inventor: Albert M. Fleischner, Westwood, NJ (US)

(73) Assignee: Vitamerica, Inc., Cedar Knolls, NJ (US)

( * ) Notice: Subject to any disclaimer, the term of this patent is extended or adjusted under 35 U.S.C. 154(b) by 0 days.

(21) Appl. No.: 09/468,819

(22) Filed: Dec. 22, 1999

(51) Int. Cl.[7] ............ A61K 31/12; A61K 31/00; A61K 33/00; A61K 35/78
(52) U.S. Cl. ............ 514/682; 426/72; 426/73; 426/74; 424/195.1; 424/600; 424/630; 424/639; 424/641; 424/646; 424/655; 424/657; 424/667; 424/670; 424/677; 424/679; 424/682; 424/702; 424/722; 424/94.1; 424/94.2; 514/52; 514/167; 514/251; 514/276; 514/277; 514/355; 514/360; 514/365; 514/387; 514/393; 514/443; 514/458; 514/474; 514/557; 514/561; 514/613; 514/646; 514/688; 514/707; 514/724; 514/725; 514/727; 514/728

(58) Field of Search .......... 426/72, 73, 74; 424/195.1, 600, 682, 630, 639, 641, 646, 655, 657, 667, 670, 677, 679, 702, 722; 514/52, 167, 251, 276, 277, 355, 360, 365, 387, 393, 443, 458, 474, 557, 561, 613, 646, 682, 688, 707, 724, 725, 727, 728

(56) References Cited

U.S. PATENT DOCUMENTS 5,846,569 * 12/1998 Anderson et al. .......... 424/535

* cited by examiner

Primary Examiner—Jose' G. Dees
Assistant Examiner—Frank Choi
(74) Attorney, Agent, or Firm—Pharmaceutical Patent Attorneys, LLC; Mark Pohl

(57) ABSTRACT

Dietary supplement compositions designed to be responsive to specific blood types, and thus most beneficial for people with specific antigenic blood types.

16 Claims, No Drawings

DIETARY SUPPLEMENTS FOR EACH SPECIFIC BLOOD TYPE

BACKGROUND

The prior art regarding this invention arises from distinct areas not heretofore combined to create new and useful formula sets or new and useful improvements thereof regarding Dietary Supplements for Each Antigen Specific Blood Type.

This invention relates to the evolving science that blood type is a mirror of the genetic code with respect to the predisposition to disease. Evidence is mounting that indicates that this predisposition to disease can be overcome through diet and nutrition.

Albert M. Fleischner, Ph.D., has a doctorate in Pharmaceutical Chemistry from Rutgers University and has had over thirty years experience in the pharmaceutical industry with firms such as Schering-Plough Corporation, Roberts Pharmaceutical Corporation, Lehn & Fink Division of Sterling Drugs, Bradley Pharmaceutical Corporation, Amerchol Division of CPC and the Goen Group companies. He has a number of published papers and a previously granted patent.

Blood is essential for life. It carries oxygen and nutrients to all parts of the body, and it carries carbon dioxide and other waste products back to the lungs, kidneys and liver for disposal.

Anthropologists have speculated that the blood types evolved due to changes in diet, culture and different environmental factors. Each blood type manifests certain particular attributes, which are characterized by strengths and weaknesses. One of the most important components, which helped determine the evolution of blood type, was what foods were available as mankind evolved.

Blood Type O is considered the original and oldest of all blood types. Years ago, animals were the main source of food. Therefore, blood type O got most of their nutrition from meat so that their diet was high in protein and low in carbohydrates. However, it was enriched with fruit and vegetables. Blood Type O's generally have higher stomach acid aiding in the digestion and metabolism of meats and most other foods. This is how our original ancestors were able to survive. People with blood type O are more prone to stomach ulcers and irritation of the stomach lining. They also have a greater resistance to blood clotting and have the thinnest blood of all blood types, as is generally known in the art. See generally, D'Adamo, P.—*Eat Right For Your Type*, G. P. Putman's Sons, 1996; D'Adamo, P.—*Cook Right For Your Type*, G. P. Putman's Sons.

The first mutation from blood type O was designated blood type A. This evolution took place because the original meat eaters migrated to areas where meat was less abundant. Thus, forcing our ancestors to survive on a diet rich in fruits and vegetables. Due to the change in diet and environment, persons with blood type A have very sensitive immune and digestive systems. These individuals normally generate lower levels of stomach acid.

The second mutation was designated blood type B. This evolved as our ancestors migrated across the many continents leading to a nomadic existence. Blood type B may have initially mutated in response to these changes in climate. People from this blood type generally have balanced immune systems and respond well to stress. They have the ability to tolerate a wide diversity of foods.

The last of the four major blood types is blood type AB. This evolved through the intermingling of type A and type B. People with this blood type have inherited the attributes of both blood type A and B. It is for this reason that their immune systems are much more complex than those of any other blood group.

The underlying differences, which characterize each known blood group, are as follows:

| Blood Type O | Blood Type A | Blood Type B | Blood Type AB |
|---|---|---|---|
| red blood cell \| | red blood cell \| A (antigen) | red blood cell \| B (antigen) | red blood cell ‖ AB (antigen) |

Our immune system contains many antigens (substances which stimulate the production of antibodies against foreign invaders). One of those antigens resides in our blood type. Each blood type contains a different antigen. The blood specific antigens are extremely important. All red blood cells contain an antigen specific for your blood type with the exception of blood type O which has no real antigenicity. This is because blood type O was the first blood type from which the others evolved. The antigen of blood type O that protrudes from the surface of our red blood cells is made up of long chains which ends in fucose. This sugar, by itself, has no antigenicity.

SUMMARY

The inventor discloses the formula sets that embody the invention of the food supplement compositions for Each Antigen Specific Blood Type that are useful in achieving and maintenance of a healthy status. The use of blood specific nutrition through diet and herbs has gained acceptance in the scientific community as a holistic approach to the promotion of wellness and the achieving and maintaining of a healthy status. Statistical studies of various diseases clearly demonstrate a predisposition based on blood type. See generally, Gillum, R. F., Blood groups, serum cholesterol, serum uric acid, blood pressure, and obesity in adolescents. J Natl Med Assoc August 1991 ; 83 (8):682–8; Wong, F. L., Kodama, K., Sasak,i H., Yamada, M., Hamilton, H. B. Longitudinal study of the association between ABO phenotype and total serum cholesterol level in a Japanese cohort. Genet Epidemiol 1992;9(6):1405–18; Whincup, P. H., Cook, D. G., Phillips, A. N., Shaper, A. G. ABO blood group and ischaemic heart disease in British men. BMJ Jun. 30, 1990; 300(6741):1679–82; George, V. T., Elston, R. C., Amos, C. I., Ward, L. J., Berenson, G. S. Association between polymorphic blood markers and risk factors for cardiovascular disease in a large pedigree. Genet Epidemiol 1987;4(4) :267–75; Voitenko, V P, Kolodchenko, V P, Poliukhov, A. M., Iushchenko, G. K. {Blood groups ABO, MN and Ph in diseases of the cardiovascular system}. Genetika 1975;11 (1):155–7; Kipschidse, N. N., Schawgulidse, N. A. {Arteriosclerosis and blood lipids}. Z Gesamte Inn Med Mar. 15, 1989; 44(6):175–6; Lee, J. S., Ro, J. Y., Sahin, A. A., Hong, W. K., Brown, B. W., Mountain, C. F., Hittelman, W. N. N Engl J Med Apr 18, 1991; 324(16):1084–90; Graziano, S. L., Tatum, A. H., Gonchoroff, N. J., Newman, N. B., Kohman, L. J. Blood group antigen A and flow cytometric analysis in resected early-sage non-small cell lung cancer. Clin Cancer Res January 1997; 3 (1):87–93; Roots, I., Drakoulis, N., Ploch, M., Heinemeyer, G., Loddenkemper, R., Minks, T., Nitz, M., Otte, F., Koch, M. Debrisoquine hydroxylation phenotype acetylation phenotype, and ABO blood groups as genetic host factors of lung cancer risk. Klin Wochenschr 1988;66 Suppl 11:87–97; Sidhu, L. S., Malhotra, P., Singh, S. P. ABO and Ph blood groups in diabetes mellitus. Anthropol Anz 1988 Step;46(3):269–75; KsenofontovIu, P. {Genetic blood markers in arthritic diseases}. Genetika Febuary 1978; 14 (2):359–64; Vioque, J., Walker, A. M. {Pancreatic cancer and ABO blood types: a study of cases and controls). Med Clin (Barc) May 25, 1991 ;96(20):761–4; Kobayashi, T., Ucida, E., Tamura, K., Yamanaka, N. The relationship between the expression of blood group-related antigens and the cell proliferation of pancreatic carcinomas induced by N-nitrosobis (2-oxopropyl) amine in hamsters. Surg Today 1993;23(10):908–16; Egami, H., Takiyama, Y., Cano, M., Houser, W. H., Pour, P. M. Establishment of hamster pancreatic ductal carcinoma cell line (PC-1) producing blood group-related antigens. Carcinogenesis May 1989:10(5);861–9; Takiyama, Y., Egami, H., Pour, P. M. Blood group antigen expression in developing pancreas and in induced pancreatic cancer cells in Syrian hamsters. Carcinogenesis April 1990;11(4):577–82; Jose, L., Nalappat, S., Sasidharan, V. P. A clinico-pathological study of carcinoma stomach. Indian J. Pathol Microbiol January 1995;38(1):73–9; Mourali, N., Muenz, L. R., Tabbane, F., Belhassen, S., Bahi, J., Levine, P. H. Epidemiologic features of rapidly progressing breast cancer in Tunisia. Cancer Dec. 15, 1980;46(12):2741–6; Marinaccio, M., Traversa, A., Carioggia, E., Valentino, L., Coviello, M., Salamanna, S., Dragone, D. C., Marinacco, L. {Blood groups of the ABO system and survival rate in gynecologic tumors}. Minerva Ginecol March 1995;47(3):69–76; Polysalov, V. N., Tarazov, P. G. {Blood group assignment-a genetic marker of hepatic hemangiomatosis}. Genetika July 1992;28(7):161–4; Kvist, E., Lauritzen, A. F., Bredesen, J., Luke, M. Relationship between blood groups and tumors of the upper urinary tract. Scand J Urol Nephrol 1988;22(4):289–91; Jia, D. X. {Bone tumor and ABO blood type}. Chung Hua Chung Liu Tsa Chih May 1991;13(3):220–22; Klechova, L., Gosheva-Antonova, T. S. {ABO and Ph blood group factors in thyroid gland diseases}. Vutr Boles 1980;19 (4):75–9; Fenlon, S., Ellis, I. O., Bell, J., Todd, J. H., Elston, C. W., Blamey, R. W. Helix pomatia and Ulex europeus lectin binding in human breast carcinoma. J Pathol July 1987;152(3):169–76; Brooks, S. A., Leathem, A. J. Prediction of lymph node involvement in breast cancer by detection of altered glycosylation in the primary tumour. Lancet Jul. 13, 1991;338(8759):71–4; Beckman, L., Angqvist, K. A. On the mechanism behind the association between ABO blood groups and gastric carcinoma. Hum Hered 1987;37 (3):140–3; Beuth, J., Ko, H. L., Tunggal, L., Pulverer, G. {Urinary tract infections caused by Staphylococcus saprophyticus. Increased incidence depending on the blood group}. Dtsch Med Wochenschr Apr 3, 1992;117(18):687–91; Runge, R. G., Pour, P. Blood group specificity of pancreatic tumor mucin. Cancer Lett October 1980;10(4):351–7.; Roath, S., Todd, C. E., Shaw, D. Transient acquired blood group B antigen associated with diverticular bowel disease. Acta Haematol 1987;77(3):188–90; Markovic, S., Bozicevic, D., Simic, D., Brzovic, Z. Genetic markers in the blood of multiple sclerosis patients. Neurol Croat 1991;41 (1–2):3–12; Darbinian, V. Zh., Nersisian, V. M., Martirosian, I. G. {Genetic markers of erythrocyte blood groups in multiple sclerosis among the American population}. Zh Nevropatol Psikhiatr 1983;83(3):42–6; Ottensooser, F., Leon, N., de Almeida, T. V. ABO blood groups and isoagglutinins in systemic lupus erythematosus. Rev Bras Pesqui Med Biol September–December 1975;8(5–6):421–5; Gekht, B. M., Agafonov, B. V., Tsuman, V. G., Shagal, D. I., Sidorova, O. P., Nalivkin, A. E. {Analysis of the association of ABO blood groups and Rhesus factor with myasthenia}. Vestn Ross Akad Med Nauk 1995; (6):16–9; Annese, V., Minervini, M., Gabbrielli, A., Gambassi, G., Manna, R. ABO blood groups and cancer of the pancreas. Int J Pancreatol March 1990;6(2):81–8; Takiyama, Y., Egami, H., Pour, P. M. Blood group antigen expression in developing pancreas and in induced pancreatic cancer cells in Syrian hamsters. Carcinogenesis April 1990;11(4):577–82; Sominina, A. A., Tsubalova, L. M., Karpova, L. S., Lipina, N. V., Nikanorov, IIu, Semilutskaia, I. B., Bekhtereva, T. A., Popova, T. L., Konovalova, N. I., Grinbaum, E. B., et al. {Genetic predisposition to latent influenza A virus in children with blood type B(III) as a possible cause of new epidemiologic strains in the countries of South-Eastern Asia}. Vestn Ross Akad Med Nauk 1994; (9):21–4; Mackenzie, J. S., Wetherall, J. D., Fimmel, P. J., Hawkins, B. R., Dawkins, R. L. Host factors and susceptibility to influenza A infection: the effect of ABO blood groups and HL-A antigens. Dev Biol Stand Jun. 1–3 1997;39:355–62; Ratner, J. J., Thomas, V. L., Forland, M. Relationships between human blood groups, bacterial pathogens, and urinary tract infections. Am J Med Sci August 1986;292(2):87–91; Sinha, A. K., Bhattacharya, S. K., Sen, D., Dutta, P., Dutta, D., Bhattacharya, M. K, Pal SC. Blood group and shigellosis. J Assoc Physicians India June 1991;39(6):452–3; Srisailapathy, C. R., Ramesh, A., Ganesan, J. Association of ABO and Rh(D) blood groups with filariasis. Hum Hered 1990;40(6):381–5; Foster, M. T. Jr, Labrum, A. H. Relation of infection with Neisseria gonorrhoeae to ABO blood groups. J infect Dis March 1976;133(3)329–30; Sidhu, L. S., Malhotra, P., Singh, S. P. ABO and Ph blood groups in diabetes mellitus. Anthropol Anz September 1998;46(3):269.75; Slipko, Z., Latuchowska, B., Wojtkowska, E. (Body structure and ABO and Rh blood groups in patients with advanced coronary heart disease after aorto-coronary by-pass surgery}. Pol Arch Med Wewn January 1994;91(1):55–60; Sapozhnikov, I. I. {Relationship between serum cholsterol content, arterial blood pressure and the ABO blood group phenotype in middle-aged men}. Kardiologiia May 1977;17(5):108–13; Takiyama, Y., Egami, H., Pour, P. M. Blood group antigen expression in developing pancreas and in induced pancreatic cancer cells in Syrian hamsters. Carcinogenesis April 1990;11(4):577–82; Shahid, A., Zuberi, S. J., Siddiqui, A. A., Waqar, M. A. Genetic markers and duodenal ulcer. JPMA J Pak Med Assoc May 1997;47(5):135–7; Escobar Castro, H., Suarez Cortina, L., Vasconez Munoz, F., Camarero Salces, C., Perdomo Giraldi, M. {Duodenal ulcer in children. Apropos of 28 cases}. Rev Esp Enferm Dig March 1990;77(3):185–8; Odeigah, P. G. Influence of blood group and secretor genes on susceptibility to duodenal ulcer. East Afr Med J July 1990;67(7):487–500; Henriksson, K., Uribe, A., Sandstedt, B., Nord, C. E. Helicobacter pylori infection, ABO blood group, and effect of misoprostol on gastroduodenal mucosa in NSAID-treated patients with rheumatoid arthritis. Dig Dis Sci September 1993;38(9):1688–96; Dzhvarisheishvili, O. G., Ksenofontov, IuP. {Genetic blood markers in occupational bronchial asthma}. Genetika 1981;17(5):906–9; Kauffmann, F., Frette, C., Pham, Q. T., Nafissi, S., Bertrand, J. P., Oriol, R. Associations of blood group-related antigens to FEVI, wheezing, and asthma. Am J Respir Crit Care Med January 1996;153(1):76–82; Ksenofontov, IuP. {Genetic blood markers in arthritic diseases}. Genetika Febuary 1978;14(2):359–64; Sostaric, V., Bozicevic, D., Brinar, V., Grbavac, Z.

Hereditary antigen characteristics of blood in ischemic cerebrovascular accident. Neurol Croat 1991;40(1):3–11; Gill, J. C., Endres-Brooks, J., Bauer, P. J., Marks, W. J. Jr, Montgomery, R. R. The effect of ABO blood group on the diagnosis of von Willebrand disease. Blood June 1987;69 (6):1691–5; Njoku, O. U., Ononogbu, I. C., Alumunan, E. O., Nwanjoh, J. Serum lipids, ABO blood group and sickle cell trait. Indian J Physiol Pharmacol April 1996;40(2) :171–4; Arato, M., Bagdy, G., Rihmer, Z., Kulcsar, Z. Reduced platelet MAO activity in healthy male students with blood group 0. Acta Psychiatr Scand February 1983;67 (2):130–4.

The solid dosage composition of these formula sets contain a series of ingredients with demonstrated nutrient activity designed to support normal form and function for each blood type. Characteristics of these constituents are generally known in the art. See, e.g., Lewis, W. H., Elvin-Lewis, M. P. F. Medical Botany, Wiley-Interscience, 1977; Claus, E. P. Pharmacognosy, Fourth Edition, Lea & Febiger, 1961; Tyler, V. E., Brady, L. R., Robbers, J. E. Pharmacognosy, Eighth Edition, Lea & Febiger, 1981; Trease, G. E., Evans, W. G. Pharmacognosy, Twelfth Edition, Bailliere Tindall, 1983; A. Y., Foster, S. Encyclopedia of Common Natural Ingredients, Second Edition, John Wiley & Sons, 1996; Balch, J. F., Balch, P. A. Prescription for Nutritional Healing, Second Edition, Avery Publishing Group, 1997.; Kalyn, W., Editor—Reader's Digest: The Healing Power of Vitamins, Minerals, and Herbs, The Reader's Digest Association, 1999. Science already knows that certain phytonutrients have demonstrated in clinical studies that they can protect against disease propensities. This invention takes that information and embodies it in a new and useful set of formulae, disclosed herein.

We now discuss in detail the most preferred versions, variants or embodiments of the invention. First, a few words on terminology. The claim term "a" includes one and more than one. The claim term "label" is used as defined in the Federal Food Drug & Cosmetic Act and the regulations promulgated thereunder. At this time, I currently lack sufficient knowledge to say whether or not Larch tree bark is safe for the claimed uses here; thus, my claims, and the claim terms "vitamin," "mineral," "herb or other botanical," "amino acid," "dietary substance" and "concentrate, metabolite, constituent, extract or combination of these ingredients" accordingly do not encompass Larch bark powder nor the butyrate derivative thereof. We now turn to discussing in great detail the best (or "preferred") versions (or "embodiments") of my invention. The composition of each unit of the Type O dietary supplement includes any combination of the specified range of the following ingredients:

| | |
|---|---|
| Vitamin K (as phytonadione) | 0 mcg–80 mcg |
| Green tea leaf extract (36% catechin & polyphenols) | 50 mg–200 mg |
| Hawthorn berry standardized extract (5% flavonoids) | 25 mg–200 mg |
| Pancreatin 4X | 50 mg–200 mg |
| Slippery elm bark | 10 mg–50 mg |
| Linden flower | 10 mg–50 mg |
| Sarsaparilla root | 10 mg–50 mg |
| Peppermint leaf | 10 mg–50 mg |
| Ginger root | 10 mg–100 mg |
| Fenugreek seed | 10 mg–50 mg |
| Parsley leaf | 10 mg–50 mg |
| Mulberry fruit | 10 mg–50 mg |
| Hops strobile | 10 mg–50 mg |
| Cayenne Pepper | 1 mg–25 mg |

-continued

| | |
|---|---|
| Deglycyrrhizinated licorice root extract | 25 mg–200 mg |
| Dandelion root | 10 mg–100 mg |
| Quercetin dihydrate | 50 mg–250 mg |
| Bladderwrack kelp | 10 mg–30 mg |

A representative formula for blood Type O is as follows, one tablet contains:

| | |
|---|---|
| Vitamin K (as phytondione) | 80 mcg |
| Green tea leaf extract (36% catechin & polyphenols) | 100 mg |
| Hawthorn berry standardized extract | 100 mg |
| Pancreatin 4X | 100 mg |
| Slippery elm bark | 50 mg |
| Linden flower | 50 mg |
| Sarsaparilla root | 50 mg |
| Peppermint leaf | 50 mg |
| Ginger root | 50 mg |
| Fenugreek seed | 40 mg |
| Parsley leaf | 25 mg |
| Mulberry fruit | 25 mg |
| Hops strobile | 25 mg |
| Cayenne Pepper | 25 mg |
| Deglycrrhizinated licorice root extract | 200 mg |
| Dandelion root | 100 mg |
| Quercetin dihydrate | 100 mg |
| Bladderwrack kelp | 300 mg |

The scientific rationale for the formulation is as follows:

Vitamin K assists in the normal clotting of blood, which is beneficial for people with blood type O, since they have fewer clotting factors in their blood. It is necessary for bone formation and repair, and for the promotion of healthy liver functions.

Green tea leaf extract may lower the risk of cancer by neutralizing and protecting cells against mutation from cancer causing agents, and by protecting against free radical damage. The antioxidant effect of green tea may protect against cardiovascular diseases and it lowers cholesterol levels. It also helps fight mental fatigue and promote longevity.

Hawthorn berry is a cardiovascular tonic. It dilates the blood vessels, which helps the blood flow through the arteries and lowers high blood pressure. The herb helps the heart pump more efficiently and it may help lower cholesterol levels.

Pancreatin 4X are enzymes that help digest and absorb foods. These enzymes are 4 times stronger than the usual USP standard. They are beneficial for ulcers, colitis, and Crohn's disease, all medical conditions linked to people with blood type O.

Slipper elm bark and Deglycyrrhizinated licorice root soothe inflamed mucous membranes (demulcent effect) of the stomach, bowel, and urinary tract. Both herbs are beneficial for heartburn, ulcers, and other digestive disorders such as colitis or Crohn's disease.

Linden flower provides support to the circulatory system, thus improving blood circulation. It is believed to help reduce stress and muscle tension, having a calming effect on the nervous system. In some instances, the herb helps to lower blood pressure.

Sarsaparilla root increases energy and, possibly, sexual stamina. It protects against harm from radiation exposure and regulates hormonal levels. The herb has diuretic properties, helping the kidneys rid the body of excess uric acid.

Peppermint leaf and Hops strobile aid in healthy digestion by assisting in the relaxation of the muscles of the digestive tract. The herbs stimulate gastric juices and the stomach lining, thus allowing food to be digested more efficiently, providing more support to the blood type o digestive system.

Ginger root is antioxidant that stimulates the immune system and aids in healthy digestion. It increases stomach acid secretion, cleanses the colon, and stimulates circulation. The herb has anti-inflammatory properties that may help alleviate pain in those suffering with inflammatory diseases of the joints, a blood type O medical risk.

Fenugreek seed has been used for centuries for digestive problems. It acts as a laxative and lubricates the intestine. It may have a mild anti-inflammatory effect making it effective for arthritis symptoms. The herb may also reduce cholesterol levels and help diabetic symptoms.

Parsley leaf contains a substance that helps prevent the multiplication of tumor cells, and is used as a digestive aid. The herb is good for high blood pressure and asthma, a condition associated with blood type O. It is also helpful for congestive heart failure and kidney disease.

Mulberry fruit helps to increase stamina.

Cayenne Pepper has analgesic activity and promotes proper blood circulation. It soothes the digestive tract and helps relieve ulcers making it a beneficial herb for the person with blood type O.

Dandelion root acts as a diuretic and is useful for treating liver and digestive problems. The herb cleanses the bloodstream and liver and increases the production of bile. It assists the pancreas and seems valuable in hypoglycemia and diabetic conditions. It is good for anemia, high cholesterol, and congestive hear failure, and may aid in the prevention of breast cancer. Dandelion is more than just a weed!

Quercetin dihydrate is a powerful antioxidant. It helps strengthen cell membranes and stops free radical from causing damage to the body. It may reduce the risk of heart disease, certain cancers, and it lowers cholesterol levels. It is a good immune booster, acts as an antihistamine (good for allergy sufferers), and has the ability to reduce inflammation (good for asthma sufferers). This bioflavonoid is also known to reduce the risk of having a stroke, a medical risk for those with blood type O.

Bladderwrack kelp helps to regulate thyroid functions, as it is a source of iodine. Iodine is necessary to regulate hormone production. Low levels of thyroid hormone lead to hypothyroidism, a type O medical risk. It is necessary for maintaining normal metabolism in cells. It is also believed to relieve rheumatoid arthritis, and boost energy and immunity.

The solid dosage composition of each unit of the Type A dietary supplement includes any combination of the specified range of the following ingredients:

| | |
|---|---|
| Vitamin C (as Ester-C calcium ascorbate) | 50 mg–500 mg |
| Vitamin E (as d-alpha-tocopheryl succinate and 50% from natural d-alpha-, and d-beta, d-gamma-, and d-delta-tocopherols) | 25 IU–400 IU |
| Folate (as folic acid) | 100 mcg–400 mcg |
| Vitamin B-12 (as cyanocobalamin) | 10 mcg–50 mcg |

Hawthorn berry standardized extract (5% flavornoids)
25 mg–200 mg
Quercetin dihydrate
50 mg–250 mg
Milk thistle seed extract (80% silymarin)
50 mg–200 mg
Alfalfa leaf
10 mg–50 mg
Aloe vera leaf gel 200:1 concentrate
10 mg–50 mg
Burdock root
10 mg–100 mg
Fenugreek seed
10 mg–50 mg
Ginger root
10 mg–100 mg
Green tea leaf extract (36% catechin & polyphenols)
50 mg–200 mg
St. John's Wort standardized extract
(0. 3% hypercin) (aerial parts)
25 mg–300 mg
Slippery elm bark
10 mg–50 mg
Skull cap root
10 mg–50 mg
Parsley leaf
10 mg–50 mg
Dandelion root
10 mg–100 mg
Chamomile flower
10 mg–50 mg
Sarsaparilla root
10 mg–50 mg
Pueraria root extract (40% soy isoflavones)
25 mg–100 mg A representative formula for blood Type A is as follows, one tablet contains:

| | |
|---|---|
| Vitamin C (as Ester-C calcium ascorbate) | 500 mg |
| Vitamin E (as d-alpha-tocopheryl succinate and 50% natural d-alpha, d-beta, d-gamma, and d-delta-tocopherols) | 200 IU |
| Folate (as folic acid) | 400 mcg |
| Vitamin B-12 (as cyanocobalamin) | 50 mcg |
| Hawthorn berry standardized extract (5% flavonoids) | 150 mg |
| Quercetin dihydrate | 120 mg |
| Milk thistle seed extract (80% silymarin) | 100 mg |
| Alfalfa leaf | 25 mg |
| Aloe vera leaf gel 200:1 concentrate | 25 mg |
| Burdock root | 25 mg |
| Fenugreek seed | 25 mg |
| Ginger root | 25 mg |
| Green tea leaf extract (36% catechin & polyphenols) | 50 mg |
| St. John's Wort standardized extract (0.3% hypercin) (aerial parts) | 50 mg |
| Slippery elm bark | 25 mg |
| Skull cap root | 25 mg |
| Parsley leaf | 25 mg |
| Dandelion root | 25 mg |
| Chamomile flower | 25 mg |
| Sarsaparilla root | 25 mg |
| Pueraria root extract (40% soy isoflavones) | 50 mg |

The scientific rationale for the formulation is as follows:
Vitamin C (as Ester-C) plays a major role in immunity and acts as an antioxidant, protecting against damage that may lead to heart disease or cancer. It may reduce cholesterol levels by increasing the level of protective HDL cholesterol. Heart disease, cancer, and high cholesterol levels are medical risks associated with people with blood type A.

Vitamin E acts as an antioxidant, helping to reduce plaque buildup on artery walls, thereby lowering cholesterol levels and risk of heart disease. It helps improve circulation and promotes normal clotting and healing which is good for the thick blood of a person with blood type A. It is also helpful in people afflicted with cancer.

Folate is necessary for red blood cell production, growth and reproduction. It is good for anemia, a blood type A risk. Also, folate is necessary for reducing homocysteine, an amino acid by-product linked to an increased risk of heart disease.

Vitamin B12 is necessary for healthy blood and promotes normal growth and development. It is needed for proper digestion, absorption of foods, protein synthesis, and carbohydrate and fat metabolism. Since B12 is usually found in animal protein, a deficiency can occur in vegans (vegetarians who also avoid dairy and eggs), and can lead to anemia.

Hawthorn berry is a cardiovascular tonic. It dilates the blood vessels, which helps the blood flow through the arteries and lowers high blood pressure. This beneficial herb for the person with blood type A helps the heart pump more efficiently and may help lower cholesterol levels.

Quercetin dehydrate is a powerful antioxidant. It helps strengthen cell membranes and stops free radicals from causing damage to the body. It may reduce the risk of heart disease, certain cancers, and it lowers cholesterol levels. This bioflavonoid is a good immune booster, acts as an antihistamine, and has the ability to reduce inflammation. It may also be good for diabetes and is overall advantageous for proper health in the blood type A person.

Milk thistle seed extract is an antioxidant, protecting liver cells and preventing damage from free radicals. It may aid in the treatment and prevention of gallstones. This herb is good for the blood type A person since they are at a risk for liver and gallbladder problems. Milk thistle may also help reduce cholesterol levels.

Alfalfa leaf acts as a diuretic and is an immune system booster, which is good for the sensitive immune system of a blood type A individual. The herb promotes proper pituitary gland functions and is beneficial for digestive disorders, high cholesterol and treating anemia. It may also help thin the blood, which is good for the thick blood of the blood type A person, and may aid in cancer prevention.

Aloe vera leaf gel provides relief from heartburn, ulcers, and other stomach disorders. It is known to soothe stomach irritation and aid in healing which is necessary for the sensitive digestive system in the person with blood type A.

Burdock root stimulates the immune system, which is good for the blood type A's immune system. The herb purifies the blood, and restores liver and gallbladder functions.

Fenugreek seed has been used for centuries for digestive problems. It acts as a laxative and lubricates the intestine. It may have a mild anti-inflammatory effect, reduce cholesterol levels, and help diabetic symptoms, making it good for the health of a person who is blood type A.

Ginger root is an antioxidant that stimulates the immune system and aids in healthy digestion. It increases stomach and secretion and cleanses the colon. The herb has anti-inflammatory properties, stimulates circulation, and is good for lowering cholesterol levels. It is beneficial herb for the person with blood type A.

Green tea leaf extract may lower the risk of cancer by neutralizing and protecting cells against mutation from causing agents, and by protecting against free radical damage. The antioxidant effect of green tea may help protect against cardiovascular diseases and it lowers cholesterol levels. It also helps fight mental fatigue and promotes longevity. An excellent herb for good health in people with type A blood. St. John's Wort acts as a natural antidepressant and may have pain-relieving effects. The herb helps fight bacteria and viruses as well as boosting the immune system.

Slippery elm bark aids in digestion since it soothes inflamed mucous membranes (demulcent effect) of the bowels, urinary tract, and stomach. It is good for heartburn, ulcers, and inflammatory bowel disease. The herb may help increase stomach acid secretions, a function that is beneficial to the blood type A's normally low stomach acid content.

Skull cap root is a safe and reliable nerve sedative. It relieves stress and improves circulation. The herb strengthens the heart muscle and is good for cardiovascular disease and lowering cholesterol levels, medical conditions that are linked to people with blood type A.

Parsley leaf contains a substance that helps prevent the multiplication of tumor cells, and is used as a digestive aid. It is also good for high blood pressure, asthma, congestive heart failure, and kidney disease.

Dandelion root acts as a diuretic and is useful for treating liver and digestive problems. The herb cleanses the bloodstream and liver and increases the production of bile. It assists the pancreases and seems valuable in hypoglycemia and diabetic conditions. It is good for anemia, high cholesterol, and congestive heart failure, and may aid in the prevention of breast cancer.

Chamomile calms the nervous system, which is good for the blood type A person, since they tend to react negatively to stress. The herb relaxes the digestive tract, speeds the healing process, and has anti-inflammatory and infection fighting properties. It is also an immune system stimulant.

Sarsaparilla root increases energy and, possibly, sexual stamina. It protects against harm from radiation exposure and regulates hormonal levels. The herb has diuretic properties, helping the kidneys rid the body of excess uric acid.

Pueraria root extract is used for cardiovascular problems by dilating coronary and cerebral vessels, and increasing blood flow and blood oxygen supply. It also helps to decrease blood pressure and lower cholesterol levels.

A solid dosage composition of each unit of the Type B dietary supplement includes any combination of the specified range of the following ingredients:

| | |
|---|---|
| Vitamin C (as Ester-C calcium ascorbate) | 50 mg–500 mg |
| Magnesium (as magnesium oxide & magnesium chloride) | 50 mg–150 mg |
| Quercetin dihydrate | 50 mg–250 mg |
| Lecithin | 50 mg–300 mg |
| Ginkgo biloba leaf extract (24% ginkgo flavonglycosides, 6% sesquiterpene lactones) | 25 mg–75 mg |
| Deglycyrrhizinated licorice root | 25 mg–200 mg |
| Hawthorn berry standardized extract (5% flavonoids) | 25 mg–200 mg |
| Burdock root | 10 mg–100 mg |
| Dandelion root | 10 mg–100 mg |
| Green tea leaf extract (36% catechin & polyphenols) | 50 ng–200 mg |
| Chamomile flower | 10 mg–50 mg |
| St. John's Wort standardized extract (0.3% hypericin) (aerial parts) | 25 mg–300 mg |
| Elderberry fruit extract | 10 mg–50 mg |
| Sarsaparilla root | 10 mg–50 mg |
| Parsley leaf | 10 mg–50 mg |

-continued

| | |
|---|---|
| Raspberry leaf | 10 mg–50 mg |
| Ginseng root extract (4–5% ginsenosides) | 50 mg–100 mg |
| Sage leaf | 10 mg–50 mg |
| Ginger root | 10 mg–50 mg |

A representative formula for blood type B is as follows, one tablet contains:

| | |
|---|---|
| Vitamin C (as Ester-C calcium ascorbate) | 250 mg |
| Magnesium (as magnesium oxide and magnesium chloride) | 128 mg |
| Quercetin dihydrate | 120 mg |
| Lecithin | 100 mg |
| Ginkgo biloba leaf extract (24% ginkgo flavonglyconsides, 6% sesquiterpene lactones) | 60 mg |
| Deglycyrrhizinated licorice root | 200 mg |
| Hawthorn berry standardized extract 5% flavonoids) | 100 mg |
| Burdock root | 25 mg |
| Dandelion root | 25 mg |
| Green tea leaf extract (36% catechin & polyphenols) | 100 mg |
| Chamomile flower | 25 mg |
| St. John's Wort standardized extract (0.3% hypericin) (aerial parts) | 50 mg |
| Elderberry fruit extract | 25 mg |
| Sarsaparilla root | 25 mg |
| Parsley leaf | 25 mg |
| Raspberry leaf | 25 mg |
| Ginseng root extract (4–5% ginsenosides) | 100 mg |
| Sage leaf | 25 mg |
| Ginger root | 25 mg |

The scientific rationale for the formulation is as follows:

Vitamin C (as Ester-C) plays a major role in immunity. Chronic fatigue syndrome may be due to weakened immune system thereby making the vitamin, and its immune boosting properties, necessary for the blood type B person. The vitamin acts as an antioxidant, which may relieve the symptoms of lupus and multiple sclerosis. It helps protect against damage that my lead to heart disease of cancer. It may also help reduce cholesterol levels by increasing the level of protective HDL cholesterol.

Magnesium is one of the most important health promoting minerals since it may help to prevent many diseases. It helps to protect against heart disease, regulates blood pressure, and fight stress. It may help with symptoms of diabetes. The mineral is needed for energy production, nerve function, muscle relaxation, and the development and proper functioning of immune cells. Magnesium may help fight muscle pains associated with chronic fatigue syndrome.

Quercetin dihydrate is a powerful antioxidant. It helps strengthen cell membranes and stops free radicals from causing damage to the body. It may reduce the risk to heart disease, certain cancers, and it lowers cholesterol levels. It is a good immune booster, acts as an antihistamine, and has the ability to reduce inflammation. This bioflavonoid may be good for diabetic conditions.

Lecithin helps build cell membranes, regulates fat metabolism, and promotes energy. It aids in lowering cholesterol and helps increase immunity against viral infections, a blood type B risk. This nutrient is essential to liver and gallbladder health.

Ginkgo biloba leaf extract has antioxidant and anti-clotting properties. The herb helps increase blood flow to the brain and in capillaries and arteries. It may decrease depression, anxiety and even slow the progression of Alzheimer's symptoms in older persons. Ginkgo may be effective in relieving symptoms of some auto immune disorders and nervous system impairments such as multiple sclerosis, as well as diabetic conditions.

Deglycyrrhizinated licorice root soothes inflamed mucous membranes (demulcent effect) of the stomach, bowel, and urinary tract. The herb is beneficial for heartburn, ulcers, and other digestive disorders such as inflammatory bowel disease, an increased risk for those with blood type B. It also has anti-viral properties and may help combat chronic fatigue syndrome.

Hawthorn berry is a cardiovascular tonic. It dilates the blood vessels, which helps the blood flow through the arteries and lowers high blood pressure. The herb helps the heart pump more efficiently and may help lower cholesterol levels. Burdock root stimulates the immune system, which is beneficial for fighting the risks of auto immune disorders in people with blood type B. The herb purifies the blood, and restores liver and gallbladder functions.

Dandelion root acts as a diuretic and is useful for treating liver and digestive problems. The herb cleanses the bloodstream and liver and increases the production of bile. It assists the pancreas and seems valuable in hypoglycemia and diabetic conditions. It is good for anemia, high cholesterol, and congestive heart failure, and may aid in the prevention of breast cancer.

Green tea leaf extract may lower the risk of cancer by neutralizing and protecting cells against mutation from cancer causing agents, and by protecting against free radical damage. The antioxidant effect of green tea may protect against cardiovascular diseases and it lowers cholesterol levels. It also helps fight mental fatigue and promotes longevity.

Chamomile calms the nervous system, relaxes the digestive tract and speeds the healing process making it beneficial for inflammatory bowel disease. It has anti-inflammatory and infection fighting properties and is an immune system stimulant.

St. John's Wort acts as a natural antidepressant and may have pain-relieving effects. The herb helps fight bacteria and viruses as well as boosting the immune system. It is an effective herb for people with blood type B.

Elderberry fruit extract has powerful antioxidant properties and helps cleanse the body. It enhances the immune system, stimulates circulation, and soothes the respiratory tract. The herb also helps alleviate the symptoms of blood type B susceptibilities to herpes simplex/cold sores, colds and influenza, and infections.

Sarsaparilla root increases energy and, possibly, sexual stamina. It protects against harm from radiation exposure and regulates hormonal levels. The herb diuretic properties, helping the kidneys rid the body of excess uric acid.

Parsley leaf contains a substance that helps prevent the multiplication of tumor cells, and is used as a digestive aid. It is good for high blood pressure, asthma, congestive heart failure, and kidney disease.

Raspberry leaf has been thought to relieve various ailments in the body. It's most prominent use has been to combat morning sickness in pregnant women in their first trimester. Raspberry leaf has also shown positive effects against diarrhea because the leaves contain tannins, which are astringent. One study actually showed that raspberry helps reduce blood sugar levels (glucose), thereby possibly having a beneficial effect on diabetes. Historically, the herb was used as a treatment for wounds and diarrhea. In 17th century England, its uses were expanded to help as an astringent against fevers, ulcers, oral and genital sores, tuberculosis, hemorrhoids, kidney stones, and to ease heavy menstrual flow in women.

Ginseng root extract (Asian/Korean) is a popular antioxidant herb used to strengthen the immune system and it protects the body against the physical effects of stress and fatigue. Properties found in ginseng help combat harmful viruses and bacteria. It also has positive effects on the nervous system. The herb may have cancer-protecting effects and may lower blood sugar levels in people with diabetes. It is a good herb for those with blood type B.

Sage leaf stimulates the central nervous system and digestive tract. It is used for indigestion, night sweats, sore throats and sore gums.

Ginger root is an antioxidant that is an immune system stimulant and aids in healthy digestion. It increases stomach acid secretion and cleanses the colon. The herb has anti-inflammatory properties, stimulates circulation, and is good for lowering cholesterol levels.

The solid dosage composition of each unit of the Type AB dietary supplement includes any combination of the specified range of the following ingredients:

| | |
|---|---|
| Vitamin C (as Ester-C calcium ascorbate) | 50 mg–500 mg |
| Hawthorn berry standardized extract (5% flavonoids) | 25 mg–200 mg |
| Siberian ginseng root extract (0.8% eleutherosides) | 10 mg–100 mg |
| Valerian root standardized extract | 5 mg–25 mg |
| Quercetin dihydrate | 50 mg–250 mg |
| Milk thistle seed extract (80% silymarin) | 50 mg–200 mg |
| Dandelion root | 10 mg–100 mg |
| Parsley leaf | 10 mg–50 mg |
| Green tea leaf extract (36% catechin & ployphenols) | 50 mg–200 mg |
| Nettle leaf extract | 10 mg–50 mg |
| St. John's Wort standardized extract (0.3% hypericin) (aerial parts) | 25 mg–300 mg |

A representative formula for blood Type AB is as follows, one tablet contains:

| | |
|---|---|
| Vitamin C (as Ester-C calcium ascorbate) | 500 mg |
| Hawthorn berry standardized extract (5% flavonoids) | 100 mg |
| Siberian ginseng root extract (0.8% eleutherosides) | 50 mg |
| Valernian root standardized extract (0.8 valerenic acid) | 10 mg |
| Quercetin dihydrate | 50 mg |
| Milk thistle seed extract (80% silymarin) | 100 mg |
| Dandelion root | 50 mg |
| Parsley leaf | 50 mg |
| Green tea leaf extract (36% catechin & polyphenols) | 100 mg |
| Nettle leaf extracts | 25 mg |
| St. John's Wort standardized extract (0.3% hypericin) (aerial parts) | 50 mg |

The scientific rationale for each formulation is as follows: Vitamin C (as Ester-C) plays a major role in immunity and acts as an antioxidant, protecting against damage that may lead to heart disease or cancer (blood type AB risks). It may also lead reduce cholesterol levels by increasing the level of protective HDL cholesterol.

Hawthorn berry is a cardiovascular tonic. It dilates the blood vessels, which helps the blood flow through the arteries and lowers high blood pressure. The herb helps the heart pump more efficiently in people with congestive heart failure and it may help lower cholesterol levels. It may be beneficial to people with blood type AB and their risk of angina.

Siberian Ginseng has elements that stimulate the immune system, which is beneficial to the weakened immune system of a person with blood type AB. The herb enhances the body's tolerance to disease, stress and fatigue. It is also useful for diabetes, a risk that may be associated with blood type AB.

Valerian root is officially approved as a sleep aid by medical authorities in European countries. The herb has been used for centuries for its calming qualities. That characteristic is beneficial to the blood type AB person since they tend to react inappropriately to stress. It has been found safe as a mild tranquilizer, is not addictive, and leaves no morning grogginess. Valerian root also helps relax the smooth muscle of the gastrointestinal tract, thereby improving the symptoms of some digestive disorders. It also helps improve circulation.

Quercetin dihydrate is powerful antioxidant. It helps strengthen cell membranes and stops free radicals from causing damage to the body. It may reduce the risk of heart disease, certain cancers, and it lowers cholesterol levels. This bioflavonoid is a good immune booster. It also acts as an antihistamine and has the ability to reduce inflammation.

Milk thistle seed extract is an antioxidant, protecting liver cells and preventing damage from free radicals. It may aid in the treatment and prevention of gallstones, a blood type AB risk, and may help reduce cholesterol levels.

Dandelion root acts as a diuretic and is useful for the blood type AB person who suffers from liver and digestive problems. The herb cleanses the bloodstream and liver and increases the production of bile. It assists the pancreas and seems valuable in hypoglycemia and diabetic conditions. It is good for anemia, high cholesterol, and congestive heart failure, and may aid in the prevention of breast cancer.

Parsley leaf contains a substance that helps prevent the multiplication of tumor cells, and is used as a digestive aid. It is good for high blood pressure, asthma, congestive heart failure, and kidney disease.

Green tea leaf extract may lower the risk of cancer by neutralizing and protecting cells against mutation from cancer causing agents, and protecting against free radical damage. The antioxidant effect of green tea may protect against cardiovascular diseases and it lowers cholesterol levels. It also helps fight mental fatigue and promotes longevity.

St. John's Wort acts as a natural antidepressant and may have pain-relieving effects. The herb helps fight bacteria and viruses as well as boosting the immune system.

Nettle leaf extract has many beneficial uses. As a dietary food, the leaves taste like spinach. They are particularly high in iron and other minerals and are rich in carotenoids and Vitamin C. It may help to relieve inflamed joints, and it also has diuretic and antihistamine properties. Nettle also helps against urinary tract infections by promoting urination, which flushes infection-causing bacteria out of the body. In some cases, it has been shown to help lower high blood pressure if caused by excess fluid in the body. However, it should only be used for this condition under the supervision of a doctor. Finally, nettle may be useful for men with enlarged prostates that are not caused by cancer by slowing prostate growth.

In addition to the blood type specific formulations for each blood type, the blood type neutral formulae is as follows:

| | |
|---|---|
| Vitamin A natural mixed carotenoids (alpha-carotene, beta-carotene, cryptoxanthin and | 5000 IU–20,000 IU |

| -continued | |
|---|---|
| lutein) | |
| Vitamin C (as Ester-C calcium ascorbate) | 50 mg–500 mg |
| Vitamin D (as cholecalciferol) | 200 IU–400 IU |
| Vitamin E (as d-alpha-tocopheryl succinate and 50% from natural d-alpha-, d-beta-, d-gamma-, and d-delta-tocopherols) | 25 IU–400 IU |
| Thiamin (as thiamin HCL) | 2.5 mg–50 mg |
| Riboflavin | 2.5 mg–50 mg |
| Niacin (as niacinamide) | 5.0 mg–50 mg |
| Vitamin B6 (as pyridoxine HCL) | 5.0 mg–50 mg |
| Folate (as folic acid) | 100 mg–400 mg |
| Vitamin B12 (as cyanocobalamin) | 10 mcg–50 mcg |
| Biotin | 100 mcg–300 mcg |
| Pantothenic acid (as D-calcium pantothenate) | 5 mg–50 mg |
| Iodine (as potassium iodine) | 50 mcg–150 mcg |
| Magnesium (as magnesium glycinate) | 25 mg–100 mg |
| Zinc (as zinc glycinate) | 7.5 mg–15 mg |
| Selenium (as selenomethionine) | 50 mcg–200 mcg |
| Copper (as copper glycinate) | 1 mg–2 mg |
| Manganese (as manganese glycinate) | 1 mg–2 mg |
| Chromium (as chromium dinicotinate) | 60 mcg–120 mcg |
| Molybdenum (as sodium molybdate) | 37.5 mcg–75 mcg |
| Chloride (as potassium chloride) | 1 mg–20 mg |
| Potassium (as potassium chloride) | 1 mg |
| Boron (as boron citrate) | 1 mg |
| Vanadium (as BMOV) | 25 mcg–50 mcg |
| Octacosanol (from rice bran) | 1,000 mcg–2,000 mcg |
| Phenalgin (phlorotannin extract - Canary Island algae) | 50 mg–100 mg |
| Alpha-lipoic acid | 5 mg–30 mg |
| Plant derived enzyme delivery system Bromelain (from Pineapple) Papain (from Papaya) | 10 mg–30 mg |

A representative formula for blood type neutral is as follows, one tablet contains:

| | |
|---|---|
| Vitamin A natural mixed carotenoids (alpha-carotene, beta-carotene, cryptoxanthin and lutein) | 10,000 IU |
| Vitamin C (as Ester-C calcium ascorbate) | 200 mg |
| Vitamin D (as cholecalciferol) | 400 IU |
| Vitamin E (as d-alpha-tocopheryl succinate and 50% from natural d-alpha-, d-beta-, d-gamma-, and d-delta-tocopherols) | 100 IU |
| Thiamin (as thiamin HCL) | 25 mg |
| Riboflavin | 25 mg |
| Niacin (as niacinamide) | 25 mg |
| Vitamin B6 (as pyridoxine HCL) | 25 mg |
| Folate (as folic acid) | 400 mcg |
| Vitamin B12 (as cyanocobalamin) | 50 mcg |
| Biotin | 300 mcg |
| Pantothenic acid (as D-calcium pantothenate) | 25 mg |
| Iodine (as potassium iodine) | 150 mcg |
| Magnesium (as magnesium glycinate) | 50 mg |
| Zinc (as zinc glycinate) | 15 mg |
| Selenium (as selenomethionine) | 200 mcg |
| Copper (as copper glycinate) | 2 mg |
| Manganese (as manganese glycinate) | 50 mg |
| Chromium (as chromium dinicotinate) | 100 mcg |
| Molybdenum (as sodium molybdate) | 75 mcg |
| Chloride (as potassium chloride) | 15 mg |
| Potassium (as potassium chloride) | 16 mg |
| Boron (as boron citrate) | 1 mg |
| Vanadium (as BMOV) | 50 mcg |
| Octacosanol (from rice bran) | 2,000 mcg |
| Phenalgin (phlorotannin extract of Canary Island algae) | 100 mg |
| Alpha-lipoic acid | 15 mg |
| Plant derived enzyme delivery system Bromelain (from Pineapple) Papain (from Papaya) | 25.5 mg |

The scientific rationale for the formulation is as follows:

Vitamin A is fat soluble, so that means that your body can store it, in the liver. Its most prominent benefit is to the retina of the eye. That's why it helps fight night blindness and helps the retina adjust to light and dark stimuli. In addition, it maintains the skin and cells that line the respiratory and gastrointestinal tracts. Also, it helps build teeth and bones, and is vital for normal reproduction, growth and development. Vitamin A has also been shown to be crucial to the immune system, including the immune cells lining the digestive tract, ultimately forming an important defense against diseases. By strengthening the immune system, it increases resistance to infections, including colds, sore throats, flu, bronchitis, warts, eye infections, cold sores and shingles, and vaginal yeast infections. It is said that Vitamin A might also help the fight against certain cancers and enhance the effectiveness of chemotherapy.

Vitamin C has many uses, mostly as an immune booster. For one, it strengthens capillaries and cell walls, and aids in the formation of collagen. This, in turn, prevents bruising, promotes healing, and keeps ligaments, tendons, and gums strong and healthy. It is also a strong antioxidant, and so it offers protection against cancer and heart disease. Furthermore, Vitamin C helps against cataracts. But perhaps the most well known use of this vitamin is its ability to shorten the duration of the cold itself.

Vitamin D is sometimes called the "sunshine vitamin" because limited exposure to the sun's UV rays invokes the production of it in the body. Its primary function is to help the body efficiently absorb calcium and phosphorous, thus helping prevent osteoporosis.

Vitamin E is yet another fat-soluble vitamin. Its basic function is to protect cell membranes. Because it acts as an antioxidant, it prevents heart disease, cancer and has been shown to lower LDL ("bad") cholesterol levels. In addition, it helps the body to use Selenium and Vitamin K more efficiently.

Thiamin (a.k.a. Vitamin B1) is a B-complex vitamin. It is essential in the conversion of carbohydrates into energy. It also plays a key role in promoting healthy nerves, thus significantly reducing numbness and tingling of the hands and feet, and may be useful in treating certain types of heart disease, such as congestive heart failure, by improving the pumping power of the heart.

Riboflavin is yet another B-complex vitamin, B2. Its primary roles are in converting proteins, fats, and carbohydrates from foods into substance forms the body can use. In addition, it plays a vital role in the production of the thyroid hormone. It also aids the body in producing infection-fighting immune cells and works with other nutrients to produce healthy, new red blood cells. In addition, it converts Vitamin B6 and niacin into active forms so they can carry out their functions in the body.

Niacin, a.k.a. Vitamin B3, is necessary in many functions of the body. For instance, it helps to release the energy from carbohydrates, control blood sugar levels, keep skin healthy, and maintain proper functioning of the nervous and digestive systems. In high enough doses, it helps to lower LDL ("bad") cholesterol and raise HDL ("good") cholesterol levels.

Vitamin B6 aids in performing numerous tasks in the body, such as forming red blood cells, making proteins, manufacturing brain chemicals such as Serotonin, maintaining nerve health, and releasing stored forms of energy. Acting as a coenzyme, this vitamin may also play a role against fighting diseases. For instance, working with folic acid, it helps to combat heart disease. Additionally, it helps to alleviate some PMS symptoms by clearing away excess levels of estrogen from the body. By acting as a building block for neurotransmitters, Vitamin B6 may prevent against epileptic seizures and perhaps even lift depression.

Folate, most often called folic acid, is vital for every function in the body that requires cell division (i.e. make blood cells, heal wounds, and build muscle). It is also necessary for the formation of DNA and RNA, assuring that the cells duplicate normally, and it produces key chemicals for the brain and nervous system. But above all, it regulates the production and existing levels of homocysteine, an amino acid that high levels of could leave the body susceptible to plague build-up in the arteries, as well as other diseases.

Vitamin B12, a.k.a. cobalamin, is the only B vitamin that the body stores in large amounts, in the liver. B12 is important for cell replication and especially important for red blood cell production. It forms a protective layer around nerves, aids in the food conversion process, and assists in the production of DNA and RNA.

Biotin helps the body use glucose more efficiently, as well as strengthening hair and nails. Additionally, because of its positive effect on blood sugar levels and the way the body responds to insulin, it has also proven to be beneficial for diabetics.

Pantothenic Acid, or Vitamin B5, is also involved in the breakdown of nutrients from food into forms the body can use. In addition, it is sometimes referred to as the "anti stress vitamin" because it plays a key role in the regulation of stress hormones. As a result, it helps in quitting smoking, migraines, and chronic fatigue syndrome. Additionally, Pantothenic Acid is useful for heartburn and helps reduce nasal congestion due to allergies.

Iodine is an essential mineral most useful for regulation of the Thyroid gland. This is vital because thyroid hormones regulate normal growth and development and metabolism in all body cells. In addition, it may assist in the treatment of fibrocystic breasts.

Magnesium is involved in many important bodily functions. These include energy production, muscle relaxation, and bone and tooth formulation. It also helps to protect against heart disease and irregular heartbeats (arrhythmia), eases fibromyalgia symptoms, lowers high blood pressure, improves some PMS symptoms, and aids in preventing complications of diabetes.

Zinc is an essential mineral that is vital to the human body. It plays many roles, aiding in various processes, including boosting the immune system and helping the body fight colds and flu. Zinc helps cell growth, sexual maturity, skin maladies, and digestive ailments. In addition, it helps to treat a vast range of chronic illnesses, including rheumatoid arthritis, under active thyroid, fibromyalgia, and osteoporosis. It has been suggested that it may boost fertility, strengthen hair, and abate Tinnitus (constant ringing in the ears). Finally, it has been referred to as a healing mineral; wounds have been proven to heal faster when there is an adequate level of Zinc in the body.

Selenium's main attribute is that it acts an antioxidant. Playing this role, it works with other vitamins to help protect against heart disease and cancer, especially cancers of the ovaries, cervix, rectum, bladder, esophagus, pancreas, and liver, as well as against leukemia. It protects the heart by making the blood less adhesive to artery walls, thus less likely to clot. Selenium protects against cataracts and macular degeneration. Furthermore, it combats viral infections, reduces the severity of cold sores and shingles, relieves lupus symptoms, and may help decelerate the progression of HIV into full-blown AIDS.

Copper plays a fundamental role in strengthening blood vessels, bones, tendons, and nerves. It helps to maintain fertility ensures healthy hair and skin pigmentation and promotes normal blood clotting. In addition, it helps prevent high blood pressure and arrhythmia, acts as an antioxidant, protecting against cancer, and is necessary for the production of many enzymes. Lack of Copper can lead to diarrhea, thyroid problems, stunted growth, mental and emotional problems, and high cholesterol.

Manganese is considered to be a trace mineral that plays a role in the metabolism of fat and protein. In this way, it is used in the nutrient conversion process. Additionally, it is an essential tool for a strong immune system, healthy nerves, normal bone growth, the regulation of blood sugar levels, and for reproduction.

Chromium is also a trace mineral. This means that the body needs it, though not in significant amounts. Chromium helps the body use insulin efficiently, and so is helpful for diabetics. It is also essential for the breakdown of fats, proteins, and carbohydrates. Additional suggested uses of this mineral are that it may help lower LDL levels of cholesterol and aid in weight loss.

Molybdenum basically serves as a coenzyme. It assists in the formation of bones and other tissues, in growth and development, the composition of DNA, and in burning fats and carbohydrates. But its primary role is that it helps the body use its stores of iron more efficiently.

Chloride in the body attracts extra cellular fluid. In addition, it helps form hydrochloric acid in the stomach. HCl is also used to aid the immune system's white cells battle foreign invaders. In addition, proper nerve function also relies on chloride.

Potassium is an essential mineral that is also an electrolyte. This means that it takes on a positive or negative charge when mixed in the bloodstream medium. Because of this particular characteristic, Potassium is useful for the regulation of fluid balance between cells, the normal behavior of nerve transmissions, of blood pressure and of heartbeats. Also, it plays a role in converting glucose into glycogen (a stored form of energy).

Boron is considered to be a trace mineral, but it plays an important role in building strong teeth, bones and nails. It may prevent calcium loss and triggers the production of estrogen, thus making bones stronger. It is useful in the metabolism of other nutrients such as calcium, magnesium, and phosphorous. The mineral has been proven to help maintain proper brain function and heightens perceptiveness. However, Boron is best for older people because of its aid against osteoporosis.

Vanadium is an ultra-trace mineral that is needed for cellular metabolism and for the formation of bones and teeth. It plays a role in growth and reproduction, and inhibits cholesterol synthesis.

Octacosanol is a nutrient that is extracted from wheat germ. It has been proven to increase oxygen utilization during exercise and improve glycogen storage in muscle. As a result, it increases physical endurance, improves reaction time, reduces high-altitude stress, and aids in tissue oxygenation. This substance can greatly benefit those who have a lowered endurance level, and is good for muscular dystrophies and other neuromuscular disorders. It also reduces blood cholesterol levels.

PHENALGIN (™) is a nutrient composed of phlorotannin extract from Canary Island algae. It serves as an antioxidant, cleaning up roaming free radicals and thus protecting against ailments such as heart disease and cancer.

Alpha-lipoic acid acts as a coenzyme to the B-complex vitamins, assisting them in the metabolism of nutrients like fats, carbohydrates and proteins, and helping them to store these until they are needed for energy. It is also a cell protector, acting as an antioxidant, as well as a catalyst in recycling other antioxidants, such as Vitamins C and E. In this way, it helps to increase their potencies. Its primary usage is to protect against nerve damage, including diabetic neuropathy. Furthermore, it helps to fortify the liver, protecting it against decrepitude from hepatitis, alcohol abuse, or exposure to poisonous or toxic chemicals. In addition, it aids in the prevention of cataracts.

Plant derived enzyme delivery system—Bromelain is a protein-digesting enzyme extracted from pineapples. It is most often used as an anti-inflammatory in the following cases: back pain, Carpel Tunnelitis, chronic pain, cuts and scrapes, gout pain, insect bites and stings, muscle aches and pains, rheumatoid arthritis, and general sprains and strains. Used with the herb tumeric, it enhances its absorption, which helps block the reproduction of HIV cells. In addition, it also serves as an anticoagulant, intensifying the thinning effect of blood.

Papain is a nutrient extracted from papaya. It serves the primary function of a digestive aid. However, its historical uses include the treatment of: infected wounds, sores, ulcers, chronic diarrhea, tumors, hay fever, esophageal obstruction due to meat impaction, catarrh, and psoriasis. Additional uses for this proteolitic enzyme is to reduce edema and inflammation associated with surgical or accidental trauma, infections, or allergies.

Without further elaboration, it is believed that one skilled in the art can, using the preceding description, utilize the present invention to its fullest extent. The specific formulas are included as a preferred embodiment of the composition formula ranges, and not to further qualify the description. Claim references to specific components include the component itself, as well as concentrates, metabolites, constituents, extracts or combinations of said ingredients.

I claim:

1. A composition of matter intended to supplement the diet,
   (a) said cormposition of matter containg, the following ingredients: Vitamin K, ginseng root, Green tea leaf, Hawthorn berry, Pancceatin, Slippery elm Dark, Linden flower, Sarsapailla root, Peppernmint leaf, Gingae root, Fenugreek seed, Parsley leaf, MulDerry fruit, Hops strobile, Cayenne Pepper, licorice root, Dandelion root, Quercetin dihydrate, and Bladderwrack kelp.
   (b) said composition of matter intended for ingestion in pill, capsule, table or liquid form;
   (c) said composition of matter not represented for use as a conventional food or as the sole item of a meal or diet;
   (d) said composition of matter labeled as a dietary supplement for use in or by humans, and
   (e) said composition of matter labeled for use by humans haring at least one specific antigen blood type, as defined by blood antigen specificity.

2. The dietary supplement of claim 1 wherein the following ingredients are present in the following approximate amounts:

| | |
|---|---|
| Vitamin K | up to 80 mcg |
| Green tea leaf | 50 mg–200 mg |
| Hawthorn berry | 25 mg–200 mg |
| Pancreatin | 50 mg–200 mg |
| Slippery elm bark | 10 mg–50 mg |
| Linden flower | 10 mg–50 mg |
| Sarsaparilla root | 10 mg–50 mg |
| Peppermint leaf | 10 mg–50 mg |
| Ginger root | 10 mg–100 mg |
| Fenugreek seed | 10 mg–50 mg |
| Parsley leaf | 10 mg–50 mg |
| Mulberry fruit | 10 mg–50 mg |
| Hops strobile | 10 mg–50 mg |
| Cayenne Pepper | 1 mg–25 mg |
| licorice root | 25 mg–200 mg |
| Dandelion root | 10 mg–100 mg |
| Quercetin dihydrate | 50 mg–250 mg |
| Bladderwrack kelp | 10 mg–30 mg. |

3. The dietary supplement according to claim 2, wherein the following ingredients are present in the following approximate amounts:

| | |
|---|---|
| Vitamin K | 80 mcg |
| Green tea leaf | 100 mg |
| Hawthorn berry | 100 mg |
| Pancreatin | 100 mg |
| Slippery elm bark | 50 mg |
| Linden flower | 50 mg |
| Sarsaparilla root | 50 mg |
| Peppermint leaf | 50 mg |
| Ginger root | 50 mg |
| Fenugreek seed | 40 mg |
| Parsley leaf | 25 mg |
| Mulberry fruit | 25 mg |
| Hops strobile | 25 mg |
| Cayenne Pepper | 25 mg |
| Deglycrrhizinated licorice root | 200 mg |
| Dandelion root | 100 mg |
| Quercetin dihydrate | 100 mg |
| Bladderwrack kelp | 300 mg. |

4. A composition of qratter intended to supplerrent the diet,
   (a) said composition of matter containing the following ingredients: Vitamin K, ginseng root, Vitamin C, Vitamin E, Folate, Hawthorn berry, Quiercetin dihydrate, Milk thistle seed, Alfalfa leaf, Aloe vera leaf gel, Burdock root, Fenugreek seed, Ginger root, Green tea leaf, St. John's Wort, Slippery elm bark, Skull cap root, Parsley leaf, Dandclion root, Chamumilc flower, Sarsaparilla root, and Pueraria root,
   (b) said composition of matter intended for ingestion in pill, capsule, tablet or liquid form;
   (c) said composition of matter not represented for use as a conventional food or as the sole item of a meal or diet;
   (d) said composition of matter labeled as a dietary supplemnent for use in or by humans, and
   (e) said composition of matter labeled for use by humans having at least one specific antigen blood type, as defined by blood antigen specificity.

5. The dietary supplement of claim 4 wherein the following ingredients are present in the following approximate amounts:

| | |
|---|---|
| Vitamin C | 50 mg–500 mg |
| Vitamin E | 25 IU–400 IU |
| Folate | 100 mcg–400 mcg |
| Vitamin B-12 | 10 mcg–50 mcg |
| Hawthorn berry | 25 mg–200 mg |

-continued

| | |
|---|---|
| Quercetin dihydrate | 50 mg–250 mg |
| Milk thistle seed | 50 mg–200 mg |
| Alfalfa leaf | 10 mg–50 mg |
| Aloe vera leaf gel | 10 mg–50 mg |
| Burdock root | 10 mg–100 mg |
| Fenugreek seed | 10 mg–50 mg |
| Ginger root | 10 mg–100 mg |
| Green tea leaf | 50 mg–200 mg |
| St. John's Wort | 25 mg–300 mg |
| Slippery elm bark | 10 mg–50 mg |
| Skull cap root | 10 mg–50 mg |
| Parsley leaf | 10 mg–50 mg |
| Dandelion root | 10 mg–100 mg |
| Chamomile flower | 10 mg–50 mg |
| Sarsaparilla root | 10 mg–50 mg |
| Pueraria root | 25 mg–100 mg. |

6. The dietary supplement according to claim 5, wherein the following ingredients are present in the following approximate amounts:

| | |
|---|---|
| Vitamin C | 500 mg |
| Vitamin E | 200 IU |
| Folate | 400 mcg |
| Vitamin B-12 | 50 mcg |
| Hawthorn berry | 150 mg |
| Quercetin dihydrate | 120 mg |
| Milk thistle seed | 100 mg |
| Alfalfa leaf | 25 mg |
| Aloe vera leaf gel | 25 mg |
| Burdock root | 25 mg |
| Fenugreek seed | 25 mg |
| Ginger root | 25 mg |
| Green tea leaf | 50 mg |
| St. John's Wort | 50 mg |
| Slippery elm bark | 25 mg |
| Skull cap root | 25 mg |
| Parsley leaf | 25 mg |
| Dandelion root | 25 mg |
| Chamomile flower | 25 mg |
| Sarsaparilla root | 25 mg |
| Pueraria root | 50 mg. |

7. A composition of matter intended to supplement the diet, (a) said composition of matter containing the following ingredientes: Vitamin C, Vitamin K, Ginseng root, Magnesium, Quercetin dihydrate, Letithin, Ginkgo bloof leaf, licorice root, Hawthorn berry, Burdock root, Dandelion root, Green tea leaf, Chamomile flower, St. John's Wort, Elderberry fruit, Sarsaparilla root, Parsley leaf, Raspberry leaf, Sage leaf, and Ginger, (b) said composition of matter intended for ingestion in pill, capslile, tablet or liquid form;

(c) said composition of matter not represented for use as a conventional food or as the sole item of a meal or diet;

(d) said composition of matter labeled as a dietary supplement for use in or by humans, and (e) said composition of matter labeled for use by humans having at least one specific antigen blood type, as defined by blood antigen specificity.

8. The dietary supplement of claim 7, wherein the following ingredients are present in the following approximate amounts:

| | |
|---|---|
| Vitamin C | 50 mg–500 mg |
| Magnesium | 50 mg–150 mg |
| Quercetin dihydrate | 50 mg–250 mg |
| Lecithin | 50 mg–300 mg |
| Ginkgo biloba leaf | 25 mg–75 mg |
| Deglycyrrhizinated licorice root | 25 mg–200 mg |
| Hawthorn berry | 25 mg–200 mg |
| Burdock root | 10 mg–100 mg |
| Dandelion root | 10 mg–100 mg |
| Green tea leaf | 50 mg–200 mg |
| Chamomile flower | 10 mg–50 mg |
| St. John's Wort | 25 mg–300 mg |
| Elderberry fruit | 10 mg–50 mg |
| Sarsaparilla root | 10 mg–50 mg |
| Parsley leaf | 10 mg–50 mg |
| Raspberry leaf | 10 mg–50 mg |
| Ginseng root | 50 mg–100 mg |
| Sage leaf | 10 mg–50 mg |
| Ginger root | 10 mg–50 mg. |

9. The dietary supplement of claim 8, wherein the following ingredients are present in the following approximate amounts:

| | |
|---|---|
| Vitamin C | 250 mg |
| Magnesium | 128 mg |
| Quercetin dihydrate | 120 mg |
| Lecithin | 100 mg |
| Ginkgo biloba leaf | 60 mg |
| Deglycyrrhizinated licorice root | 200 mg |
| Hawthorn berry | 100 mg |
| Burdock root | 25 mg |
| Dandelion root | 25 mg |
| Green tea leaf | 100 mg |
| Chamomile flower | 25 mg |
| St. John's Wort | 50 mg |
| Elderberry fruit | 25 mg |
| Sarsaparilla root | 25 mg |
| Parsley leaf | 25 mg |
| Raspberry leaf | 25 mg |
| Ginseng root | 100 mg |
| Sage leaf | 25 mg |
| Ginger root | 25 mg. |

10. A composition of matter intended to supplement the diet, (a) said composition of matter containing the following ingredients: Vitamin C, Vitamin K, Hawthorn berry, ginseng root, Vailerian rool:, Quercein dihydrate, Milk thistle seed, Dandelion root, Parslsey leaf, Green tea leaf, Nettle leaf, and St. John's Wort, (b) said composition of matter inended for ingestion in pill, capsule, tablet or liquid form;

(c) said composition of matter not represented for use as a conventional food or as the sole item of a meal or diet;

(d) said composition of matter labeled as a dietary supplement for uise in or by humans, and (e) said composition ot matter labeled for use by humans having at least one specific antigen blood type, as defined by blood antigen specificity.

11. The dietary supplement of claim 10, wherein the following ingredients are present in the following approximate amounts:

| | |
|---|---|
| Vitamin C | 50 mg–500 mg |
| Hawthorn berry | 25 mg–200 mg |

-continued

| | |
|---|---|
| ginseng root | 10 mg–100 mg |
| Valerian root | 5 mg–25 mg |
| Quercetin dihydrate | 50 mg–250 mg |
| Milk thistle seed | 50 mg–200 mg |
| Dandelion root | 10 mg–100 mg |
| Parsley leaf | 10 mg–50 mg |
| Green tea leaf | 50 mg–200 mg |
| Nettle leaf | 10 mg–50 mg |
| St. John's Wort | 25 mg–300 mg. |

12. The dietary supplement of claim 11, where the following ingredients are present in the following approximate amounts:

| | |
|---|---|
| Vitamin C | 500 mg |
| Hawthorn berry | 100 mg |
| Siberian ginseng root | 50 mg |
| Valernian root | 10 mg |
| Quercetin dihydrate | 50 mg |
| Milk thistle seed | 100 mg |
| Dandelion root | 50 mg |
| Parsley leaf | 50 mg |
| Green tea leaf | 100 mg |
| Nettle leaf | 25 mg |
| St. John's Wort | 50 mg. |

13. A composition of matter intended to supplement the diet,
  (a) said composition of matter containing the followirg ingredients: Vitamin K, ginsencg root, green tea leaf, Vitamin A, Vitarnin C, Vitarnin D, Vitamn E, Thiamin, Riboflavin, Niacin, vitamin B6, Folate, Vitamin B12, Biotin, Pantothenic acid, Iodine, Magnesium, Zinc, Selenium, Copper, Manganese, Chromirium, Molyhdenum, Chloride and Potassium,
  (b) said composition of matter intended for ingestion in pill, capsule, tablet or liquid form;
  (c) said composition of matter not represented for use as a conventional food or as the sole item of a meal or diet;
  (d) said composition of master labeled as a dietary supplement for use in or by humans, and
  (e) said composition of matter labeled for use by humans having at least one specific antigen blood type, as defined by blood antigen specificity.

14. The dietary supplement of claim 13, further comprising Boron, Vanadium, Octacosanol, Phenalgin, Alpha-lipoic acid, Bromelain and Papain.

15. The dietary supplement of claim 14, wherein the following ingredients are present in the following approximate amounts:

| | |
|---|---|
| Vitamin A | 5000 IU–20,000 IU |
| Vitamin C | 50 mg–500 mg |

-continued

| | |
|---|---|
| Vitamin D | 200 IU–400 IU |
| Vitamin E | 25 IU–400 IU |
| Thiamin | 2.5 mg–50 mg |
| Riboflavin | 2.5 mg–50 mg |
| Niacin | 5.0 mg–50 mg |
| Vitamin B6 | 5.0 mg–50 mg |
| Folate | 100 mg–400 mg |
| Vitamin B12 | 10 mcg–50 mcg |
| Biotin | 100 mcg–300 mcg |
| Pantothenic acid | 5 mg–50 mg |
| Iodine | 50 mcg–150 mcg |
| Magnesium | 25 mg–100 mg |
| Zinc | 7.5 mg–15 mg |
| Selenium | 50 mcg–200 mcg |
| Copper | 1 mg–2 mg |
| Manganese | 1 mg–2 mg |
| Chromium | 60 mcg–120 mcg |
| Molybdenum | 37.5 mcg–75 mcg |
| Chloride | 1 mg–20 mg |
| Potassium | 1 mg |
| Boron | 1 mg |
| Vanadium | 25 mcg–50 mcg |
| Octacosanol | 1,000 mcg–2,000 mcg |
| Phenalgin | 50 mg–100 mg |
| Alpha-lipoic acid | 5 mg–30 mg |
| Bromelain and Papain | 10 mg–30 mg. |

16. The dietary supplement of claim 15, wherein the following ingredients are present in the following approximate amounts:

| | | |
|---|---|---|
| Vitamin A natural mixed carotenoids | 10,000 | IU |
| Vitamin C | 200 | mg |
| Vitamin D | 400 | IU |
| Vitamin E | 100 | IU |
| Thiamin | 25 | mg |
| Riboflavin | 25 | mg |
| Niacin | 25 | mg |
| Vitamin B6 | 25 | mg |
| Folate | 400 | mcg |
| Vitamin B12 | 50 | mcg |
| Biotin | 300 | mcg |
| Pantothenic acid | 25 | mg |
| Iodine | 150 | mcg |
| Magnesium | 50 | mg |
| Zinc | 15 | mg |
| Selenium | 200 | mcg |
| Copper | 2 | mg |
| Manganese | 50 | mg |
| Chromium | 100 | mcg |
| Molybdenum | 75 | mcg |
| Chloride | 15 | mg |
| Potassium | 16 | mg |
| Boron | 1 | mg |
| Vanadium | 50 | mcg |
| Octacosanol | 2,000 | mcg |
| Phenalgin | 100 | mg |
| Alpha-lipoic acid | 15 | mg |
| Bromelain and Papain | 25.5 | mg. |

* * * * *